(12) United States Patent
Chung et al.

(10) Patent No.: US 9,617,543 B2
(45) Date of Patent: Apr. 11, 2017

(54) SUGAR CHAIN-CONTAINING POLYMER, AND SUGAR CHAIN-CONTAINING POLYMER COMPLEX

(71) Applicants: SOMAR Corp., Tokyo (JP); KOREAN RESEARCH INSTITUTE OF BIOSCIENCE AND BIOTECHNOLOGY, Daejeon (KR)

(72) Inventors: Bong Hyun Chung, Daejeon (KR); Hirohiko Ise, Fukuoka (JP); Toshihiro Akaike, Nishitokyo (JP); Sun-Jung Kim, Daejeon (KR)

(73) Assignees: SOMAR CORP., Tokyo (JP); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 14/287,943

(22) Filed: May 27, 2014

(65) Prior Publication Data
US 2015/0148527 A1    May 28, 2015

(30) Foreign Application Priority Data
Nov. 28, 2013 (JP) ................................ 2013-246145

(51) Int. Cl.
*A61K 47/48* (2006.01)
*A61K 49/00* (2006.01)
*C12N 15/113* (2010.01)
*C12N 15/11* (2006.01)

(52) U.S. Cl.
CPC ...... *C12N 15/1136* (2013.01); *A61K 49/0034* (2013.01); *A61K 49/0052* (2013.01); *A61K 49/0054* (2013.01); *C12N 15/111* (2013.01); *C12N 2310/14* (2013.01); *C12N 2320/32* (2013.01)

(58) Field of Classification Search
CPC ......... C07H 21/04; C07H 21/02; A61K 48/00
USPC ........................................ 536/17.4; 514/44 R
See application file for complete search history.

(56) References Cited

FOREIGN PATENT DOCUMENTS

CN        103030813 A  *  4/2013

OTHER PUBLICATIONS

Martello et al. (Protocol Exchange (2007), Published online, Sep. 3, 2007) (Abstract sent).*
Zhao et al; CN 103030813 A; Apr. 10, 2013 (Machine English Translation).*
Kim et al. (Biomaterials 32 (2011) 3471-3480).*
Ise et al., "Vimentin and desmin possess GlcNAc-binding lectin-like properties on cell surfaces," Glycobiology, vol. 20, No. 7, Mar. 22, 2010, pp. 843-864.
Kim et al., "Imaging and therapy of liver fibrosis using bioreducible polyethylenimine/siRNA complexes conjugated with N-acetylglucosamine as a targeting moiety," Biomaterials, vol. 34, May 13, 2013, pp. 6504-6514.
Komura et al., "Dynamic behaviors of vimentin induced by interaction with GlcNAc molecules," Glycobiology, vol. 22, No. 12, Jul. 30, 2012, pp. 1741-1759.

* cited by examiner

*Primary Examiner* — Shaojia Anna Jiang
*Assistant Examiner* — Michael C Henry
(74) *Attorney, Agent, or Firm* — Birch, Stewart, Kolasch & Birch, LLP (57) ABSTRACT

A sugar chain-containing polymer that enables targeting to the lesion area of liver fibrosis and is useful for imaging, diagnosis and therapy of liver fibrosis; and a sugar chain-containing polymer complex comprising the polymer as a carrier for an anionic substance useful fix therapy and the like; are provided. The polymer is a sugar chain-containing polymer which is a cationic polymer comprising an amine, which polymer comprises N-acetylglucosamine bound thereto. The polymer preferably has a disulfide bond. The polymer preferably has a structure in which polyethyleneimine is linked via a disulfide bond.

13 Claims, 8 Drawing Sheets

SUGAR CHAIN-CONTAINING POLYMER, AND SUGAR CHAIN-CONTAINING POLYMER COMPLEX

TECHNICAL FIELD

The present invention relates to a sugar chain-containing polymer and a sugar chain-containing polymer complex; more specifically, a sugar chain-containing polymer that specifically interacts with liver in liver fibrosis and is useful for imaging, diagnosis and therapy of the lesion area of liver fibrosis, and a sugar chain-containing polymer complex comprising the polymer as a carrier for an anionic substance.

BACKGROUND ART

Liver fibrosis is associated with fatal liver diseases such as liver cancer and liver cirrhosis. For preventing common liver diseases, diagnosis and therapy of liver fibrosis at an early stage is important. Activated hepatic stellate cells (HSCs) play important roles in liver fibrosis. In damaged liver, HSCs change their characters from the steady state to the active state, and induce secretion of cytokines and growth factors from hepatocytes and nonparenchymal cells. Activated HSCs also produce extracellular matrix (ECM)-constituting factors such as collagen, which contribute to liver fibrosis. Thus, targeting to activated HSCs, and delivery of a gene or agent to activated HSCs are key points of therapy of liver fibrosis.

Recently, the present inventors discovered that a polymer containing N-acetylglucosamine (GlcNAc) has strong binding ability to vimentin and desmin on the cell surface (Non-patent Documents 1 and 2). Further, the present inventors reported that an N-acetylglucosamine-containing polymer (PVGlcNAc) can identify vimentin- and desmin-positive cells from a hepatocyte population. The N-acetylglucosamine-containing polymer interacts with vimentin-positive cells such as sinusoidal endothelial cells, Kupffer cells and HSCs. In particular, activated HSCs more strongly express vimentin and desmin than HSCs in the steady state and other nonparenchymal cells. PVGlcNAc is a polymer having a structure in which N-acetylglucosamine is bound to a polystyrene backbone. The hydrophobic polystyrene chain is strongly adsorbed to a polystyrene culture dish, which is also hydrophobic. Taking advantage of this property, selective culture of specific hepatocytes became possible by preparing a PVGlcNAc-coated culture dish.

The indocyanine green (ICG) fluorescent dye is approved by FDA, and widely used for imaging and therapy of diseases. ICG has also been used for evaluation of liver function by measurement of its blood level. However, in cases where ICG alone is injected, the ICG fluorescence signal rapidly disappears from blood. In order to realize ICG imaging that can be maintained for a long period, its binding with a nanomaterial is necessary. Polymers and phospholipids have been used for stabilizing ICG in blood.

Delivery of small interfering ribonucleic acid (siRNA) is hopeful as a therapeutic method for diseases, which method is based on knockdown of a specific disease-associated gene or protein. However, degradation by enzymes, as well as incapability of siRNA to pass through the cell membrane are problematic. In order to solve these problems, many researchers have studied stable delivery systems for delivering siRNA to cells or a tissue by a method using a virus vector (for example, adenovirus or lentivirus) or a method using no virus vector (using, for example, liposomes, a cation polymer or a dendrimer).

RELATED ART DOCUMENTS

Non-Patent Documents

[Non-patent Document 1] Ise H., et al., Glycobiology 2010; 20: 843-64

[Non-patent Document 2] Komura K., Ise H., Akaike T., Glycobiology 2012; 22: 1741-59

SUMMARY OF THE INVENTION

Problems to be Solved by the Invention

As described above, early detection and therapy of liver fibrosis are important for therapy of liver diseases. Development of methods of targeting and delivery of drugs, reagents, therapeutic genes and the like to activated HSCs, and carriers therefor, as key points of therapy of liver fibrosis has been demanded.

In view of this, the present invention aims to provide a sugar chain-containing polymer that enables targeting to the lesion area of liver fibrosis and is useful for imaging, diagnosis and therapy of liver fibrosis; and a sugar chain-containing polymer complex comprising the polymer as a carrier for an anionic substance useful for therapy and the like.

Means for Solving the Problems

In order to solve the above-described problems, the present inventors intensively studied to discover that the problems can be solved by binding N-acetylglucosamine to a cationic polymer containing an amine, thereby completing the present invention.

That is, the sugar chain-containing polymer of the present invention is a cationic polymer comprising an amine, which polymer comprises N-acetylglucosamine bound thereto.

The sugar chain-containing polymer of the present invention preferably comprises a disulfide bond.

The sugar chain-containing polymer of the present invention preferably comprises a structure in which a polyethyleneimine is linked via a disulfide bond.

The sugar chain-containing polymer of the present invention preferably further comprises a fluorescent dye bound thereto.

In the sugar chain-containing polymer of the present invention, the fluorescent dye is preferably indocyanine green.

The sugar chain-containing polymer complex of the present invention is characterized in that the complex comprises the sugar chain-containing polymer of the present invention and an anionic substance(s).

In the sugar chain-containing polymer complex of the present invention, the sugar chain-containing polymer and the anionic substance(s) form a complex by electrostatic interaction.

In the sugar chain-containing polymer complex of the present invention, the anionic substance is preferably nucleic acid.

In the sugar chain-containing polymer complex of the present invention, the nucleic acid is preferably RNA.

In the sugar chain-containing polymer complex of the present invention, the RNA is preferably an siRNA.

In the sugar chain-containing polymer complex of the present invention, the siRNA is preferably an siRNA of TGFβ1.

Effect of the Invention

The present invention can provide a sugar chain-containing polymer that enables targeting to the lesion area of liver fibrosis and is useful for imaging, diagnosis and therapy of liver fibrosis; and a sugar chain-containing polymer complex comprising the polymer as a carrier for an anionic substance(s) useful for therapy and the like.

BRIEF DESCRIPTION OF THE DRAWINGS

FIG. 5A-FIG. 5C show fluorescence images of cells as observed by confocal microscopy for confirmation of uptake of FITC-conjugated siRNA/polymer complexes by the cells.

FIG. 6A-FIG. 6C show photographs showing results of in vivo imaging of ICG fluorescence.

BEST MODE FOR CARRYING OUT THE INVENTION

The sugar chain-containing polymer of the present invention is a cationic polymer comprising an amine, which polymer comprises N-acetylglucosamine bound thereto. The amine may be any of primary, secondary and tertiary amines, or may comprise all of primary to tertiary amines. Since the polymer is cationic, the polymer can form a complex with a useful anionic substance or macromolecule by electrostatic interaction.

N-acetylglucosamine binds to the polymer preferably by covalent bonding. The method of binding of N-acetylglucosamine is not limited. Examples of the method include formation of a bond by reaction of a side-chain amine in the polymer with a sugar chain having N-acetylglucosamine at its terminus. N-acetylglucosamine is preferably contained at a side-chain terminus in the polymer by a structure represented by the formula below.

The backbone of the sugar chain-containing polymer of the present invention is preferably polyethyleneimine. Polyethyleneimine is a cationic water-soluble polymer produced by polymerization of ethyleneimine. Polyethyleneimine has a structure represented by the molecular formula [—(CH$_2$CH$_2$NH—]$_n$, and is linear or branched. The polyethyleneimine is preferably linear.

The sugar chain-containing polymer of the present invention preferably has a disulfide bond, and preferably has a structure in which a plurality of polymers are bound together via a disulfide bond(s). The disulfide bond(s) is/are cleaved upon reduction. Disulfide bonds are easily reduced in intracellular environments in which glutathion is contained at high concentration. Thus, in cases where a disulfide bond(s) is/are present in the sugar chain-containing polymer, preferably in the backbone, the sugar chain-containing polymer shows excellent stability in the extracellular space while the polymer is degraded in the cell by reduction. Therefore, in cases where the polymer is forming a complex with a useful substance, the polymer can efficiently release the useful substance in the cell.

The sugar chain-containing polymer of the present invention preferably contains a fluorescent dye bound thereto. In cases where the polymer contains a fluorescent dye, specific cells can be detected and observed with fluorescence. The fluorescent dye is not limited as long as the dye can be used in the living body. Examples of the fluorescent dye include fluorescein derivatives such as fluorescein isothiocyanate (FITC); fluorescent proteins such as Calcein-AM (DOJINDO LABORATORIES), indocyanine green, GFP, RFP and YFP; and SYBR Green. Indocyanine green is preferred.

The molecular weight of the sugar chain-containing polymer of the present invention is preferably not less than 3000.

Figure 2A:
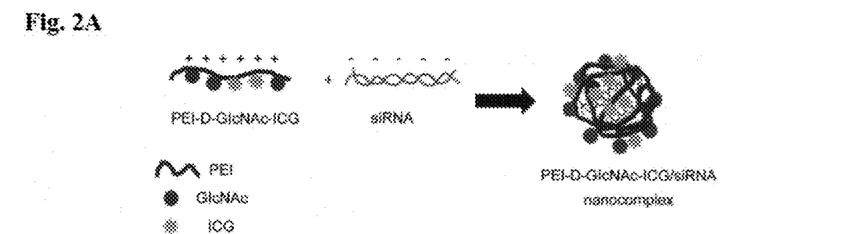
FIG. 2A is a schematic diagram illustrating formation of a complex (nanocomplex) using PEI-D-GlcNAc-ICG and siRNA.
Figure 3A:
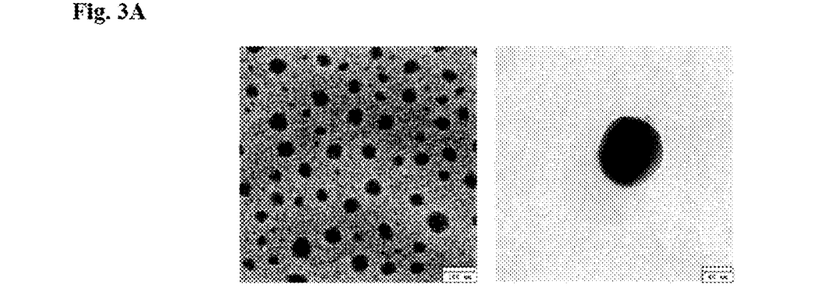
FIG. 3A shows photographs showing the shape and the size of PEI-D-GlcNAc-siRNA taken by TEM.

The sugar chain-containing polymer complex of the present invention is characterized in that the complex comprises the sugar chain-containing polymer and an anionic substance. The sugar chain-containing polymer of the present invention is cationic, and can therefore form a complex with the anionic substance by electrostatic interaction. For example, as shown in FIG. 2A and FIG. 3A, a sugar chain-containing polymer complex having a nanoparticulate shape can be formed by incorporation of an anionic siRNA. The anionic substance is preferably capable of interacting with the sugar chain-containing polymer of the present invention by electrostatic interaction to form a complex, and preferably a substance useful for therapy and/or imaging of lesions. In cases where the sugar chain-containing polymer complex has a disulfide bond, the complex is degraded by reduction in the cell, and the anionic substance contained therein is released into the cell. Further, since the sugar chain-containing polymer of the present invention contains N-acetylglucosamine, which interacts with desmin and vimentin, which are highly expressed in activated hepatic stellate cells (HSCs), specific targeting to activated stellate cells is possible. Thus, the sugar chain-containing polymer of the present invention or the complex thereof is useful as a drug delivery system (DDS) to the liver, especially hepatic stellate cells in liver fibrosis.

The anionic substance is preferably nucleic acid, more preferably RNA, still more preferably an siRNA, especially preferably an siRNA of TGFβ1. Delivery of an siRNA into specific cells is generally difficult, but the sugar chain-containing polymer complex of the present invention can efficiently deliver an siRNA into hepatic stellate cells (HSCs).

The size of the sugar chain-containing polymer complex of the present invention is preferably about 5 to 200 nm in diameter.

EXAMPLES

The present invention is described below in more detail by way of Examples. The present invention is not limited by the Examples below.

(Materials and Methods)
(Materials)

Polyethyleneimine (PEI) (0.8 KDa) was purchased from Sigma-Aldrich CO. LLC. N,N'-cystaminebisacrylamide (CBA) was purchased from Polyscience, Inc. Chitobiose was purchased from Megazyme International Ireland. 3-(4, 5-dimethylthiazol-2-yl)-2,5-diphenyl tetrazolium bromide (MTT), water-soluble carbodiimide, [1-ethyl-3,3(-dimethylaminopropyl)carbodiimide hydrochloride (EDC)], and 1,4-dithiothreitol (DTT) were purchased from Sigma-Aldrich CO. LLC. A monoclonal mouse anti-TGFβ1 antibody was purchased from R&D Systems, Inc. A monoclonal mouse anti-β-actin antibody, monoclonal mouse anti-desmin antibody, and monoclonal mouse anti-α-smooth muscle actin antibody were purchased from Sigma-Aldrich CO. LLC. A horseradish peroxidase (HRP)-conjugated mouse secondary antibody was purchased from Abcam plc. 2-[7-[1,3-Dihydro-1,1-dimethyl-3-(4-sulfobutyl)-2H-benzo[e]indol-2-ylidene]-1,3,5-heptatrienyl]-1,1-dimethyl-3-[5-(3-sulfosuccinimidyl)oxycarbonylpentyl]-1H-benzo[e]indolium (ICG-Osu) was purchased from Dojindo Molecular Technologies, Inc. A stellate cell medium was purchased from ScienCell Research Laboratories.

(Immobilization of Disulfide Bond, GlcNAc and ICG to PEI (PEI-D-GlcNAc-ICG))

A disulfide bond-conjugated polyethyleneimine (PEI-D) was obtained by Michael addition using CBA. Under nitrogen atmosphere, 0.8-KDa PEI (10% aqueous methanol) and CBA (at a molar ratio of 1:2—ratio of reactive groups in CBA to amino groups in PEI) were mixed together at 55° C. for 24 hours. Unreacted CBA was eliminated with an excess amount of PEI. The resulting product was purified using a dialysis membrane (MWCO3500). GlcNAc was immobilized to PEI-D (PEI-D-GlcNAc) by the known EDC coupling method (Kim S J., et al., Biomaterials 2011; 32: 3471-80).

For conjugating ICG to PEI-D-GlcNAc (PEI-D-GlcNAc-ICG), ICG-Osu was dissolved in dimethyl sulfoxide (1 mg/ml). An equal amount of the polymer (2 mg/ml in PBS) and ICG-Osu were mixed for 2 hours at room temperature. Unreacted ICG-Osu was eliminated by centrifugation at 15,000 rpm. Immobilization of the disulfide bond and GlcNAc was confirmed by FT-IR (Bruker Optics IF66, manufactured by Bruker Optics) and $^1$H-NMR (DU-800, manufactured by Beckman Coulter, Inc.).

(Preparation and Characterization of Complex)

siRNA and PEI-D-GlcNAc were mixed at various ratios to form complexes. To confirm the presence of the disulfide bond, DTT was added at 50 nM to the solution of each complex, and the resulting mixture was left to stand for 10 minutes at room temperature. The formation of a complex was confirmed by gel shift assay. The sample of each complex was subjected to electrophoresis in 1% agarose gel supplemented with 0.1% ethidium bromide, in a solution (TAE) containing Tris base, acetic acid, and ethylenediaminetetraacetic acid (EDTA), at 100 V for 15 minutes. To measure the size and the zeta potential, the polymer (PEI-D-GlcNAc, PEI-D-GlcNAc-ICG) and siRNA (20 times volume) were mixed together in distilled water, and the resulting mixture was left to stand for 20 minutes at room temperature. The size and the zeta potential of each complex were measured by dynamic light scattering (DLS). The fluorescence intensity of ICG in the complex after the addition of DTT was measured by a microplate reader (SpectraMax M2, manufactured by Molecular Devices Inc.) at excitation and emission wavelengths of 805 nm and 820 nm, respectively.

(Cytotoxicity)

About $1\times10^4$ cells/well of rat hepatic stellate cells (ScienCell Research Laboratories) were cultured in a 96-well cell culture plate containing a medium for stellate cells supplemented with 10% FBS and penicillin/streptomycin for 24 hours. An MTT assay was performed to estimate the cell viability. The cells were incubated with polymers at various concentrations for 24 hours. The cell culture medium was replaced, and 10 μl of an MTT solution (5 mg/ml in PBS) was added to the culture, followed by culturing the cells for 4 hours. Thereafter, the cells were washed, and the formazan dye produced was dissolved in 100 μl of dimethylsulfoxide for 15 minutes. The absorption was measured at 570 nm with a microplate reader.

(Cellular Uptake of Complex and Binding Via Desmin)

Uptake of the complexes by cells and binding via desmin were observed by confocal microscopy. HSCs at a density of $1 \times 10^4$ (cells/well) were cultured on 8-well chamber slides for 24 hours. FITC-conjugated siRNA and the synthesized polymer (PEI-D, PEI-D-GlcNAc) were incubated for 30 minutes at room temperature in a medium for stellate cells. Thereafter, the complex was incubated with the cells for 4 hours, and the cells were washed with PBS three times. The cells were then fixed using 4% paraformaldehyde for 10 minutes. The cells were permeabilized with 0.1% Triton X-100 to stain intracellular desmin. These cells were subjected to blocking therapy with 1% bovine serum albumin (BSA) for 30 minutes, and then incubated with a rabbit polyclonal desmin antibody (manufactured by Sigma-Aldrich CO. LLC) for 2 hours. Thereafter, the cells were incubated for 2 hours at room temperature with a Cy3-conjugated goat anti-mouse IgG antibody (Jackson Immuno Research Laboratories, Inc.) as a secondary antibody. Cell nuclei were stained with a 4'6-diamidino-2-phenylindole (DAPI) solution.

(Induction of Liver Fibrosis in Mice)

Carbon tetrachloride ($CCl_4$) was used for induction of liver fibrosis in mice. $CCl_4$ was dissolved in olive oil (1:5), and 1 μl/μg body weight of the $CCl_4$ solution was intraperitoneally injected to female mice (Baltic/nu) of 5 to 6 weeks old once a week for a total of 5 weeks. All animal experiments have been approved by Korea Research Institute of Bioscience and Biotechnology (KRIBB).

(Imaging and Therapy of Liver Fibrosis)

For diagnosis and therapy of liver fibrosis, the PEI-D-GlcNAc-ICG/TGFβ1 siRNA complex was intravenously injected to the mice (200 μl), and, 3 days after the first injection, the PEI-D-GlcNAc/TGFβ1 siRNA was intravenously injected to the mice. One day and two days after the injection of the complex and ICG, the mice were observed with an IVIS Lumina imaging system (Xenogen Corporation) using an ICG filter set. Seven days after the first transfection, the therapeutic effect of the PEI-D-GlcNAc-ICG/TGFβ1 siRNA complex was investigated by Western blotting and H&E staining. To perform ex vivo imaging, the mice were dissected 6 days after the injection of the complex, and the liver, spleen and kidney were observed using the imaging system.

(Western Blotting)

Proteins from cells and tissues were analyzed by Western blotting. Cells and tissues were homogenized in RIPA buffer (GenDEPOT, Inc.) and centrifuged at 13,000 rpm for 30 minutes at 4° C. The protein concentration was measured using a Bradford assay kit (GenDEPOT, Inc.). Equal amounts of proteins were separated by 12% SDS polyacrylamide gel electrophoresis (SDS-PAGE), and transferred to a PVDF membrane. The membrane was blocked with Blocking one (NACALAI TESQUE, Inc.) for 1 hour, and incubated with a primary antibody, a monoclonal mouse anti-α-SMA antibody (1:2000 dilution) or anti-β-actin antibody (1:5000 dilution), for 2 hours. The membrane was washed with TBST buffer, and incubated with an HRP-conjugated mouse secondary antibody for 2 hours at room temperature. Bands of the proteins were detected with LAS 3000 (FUJI FILM Corporation). The band intensity was analyzed using Image J software.

(Histochemical and Immunofluorescence Staining Analysis)

The liver was fixed with formalin, and embedded in paraffin to prepare samples. Hematoxylin and eosin staining (H&E staining) was performed according to a standard method. The samples were observed under a light microscope. Immunofluorescence staining was performed using cryosection specimens. The sections were blocked with 1% BSA for 1 hour, and incubated with a polyclonal rabbit anti-desmin antibody (Abcam plc) for 2 hours. The sections were then reacted with a rabbit FITC-conjugated secondary antibody for 2 hours at room temperature. The sections were observed by confocal microscopy.

(Statistical Analysis)

A plurality of independent experiments were performed, and the obtained data were expressed as the mean and the standard deviation. The results were subjected to testing by Student's t-test.

(Results and Discussion)

(Preparation of PEI-D-GlcNAc-ICG)

Figure 1A:
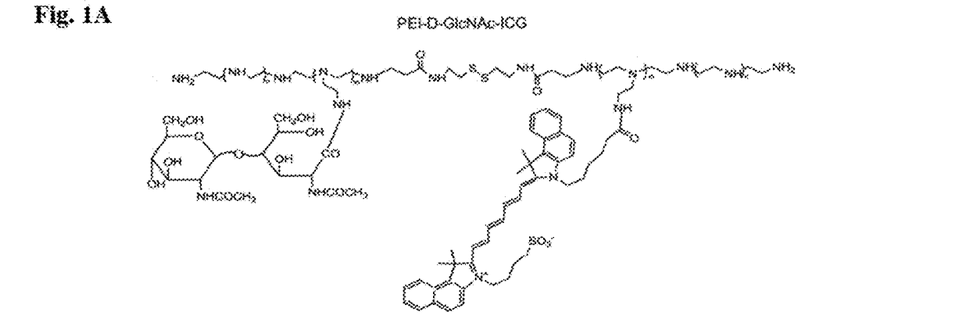
FIG. 1A is a chemical formula representing the structure of PEI-D-GlcNAc-ICG used in Examples.

For efficient targeting and imaging of liver fibrosis, N-acetyl-glucosamine and indocyanine green were immobilized on a carrier (see FIG. 1A).

Figure 1B:
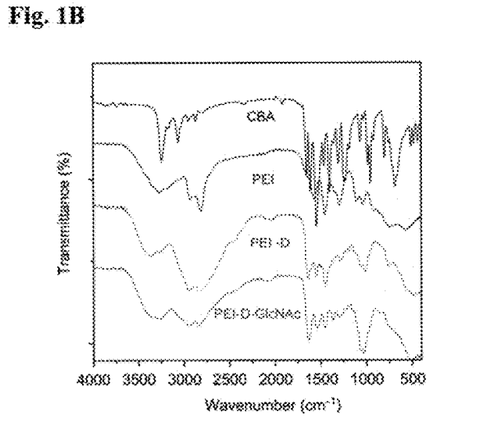
FIG. 1B shows FT-IR spectra of the polymers synthesized in Example.
Figure 1C:
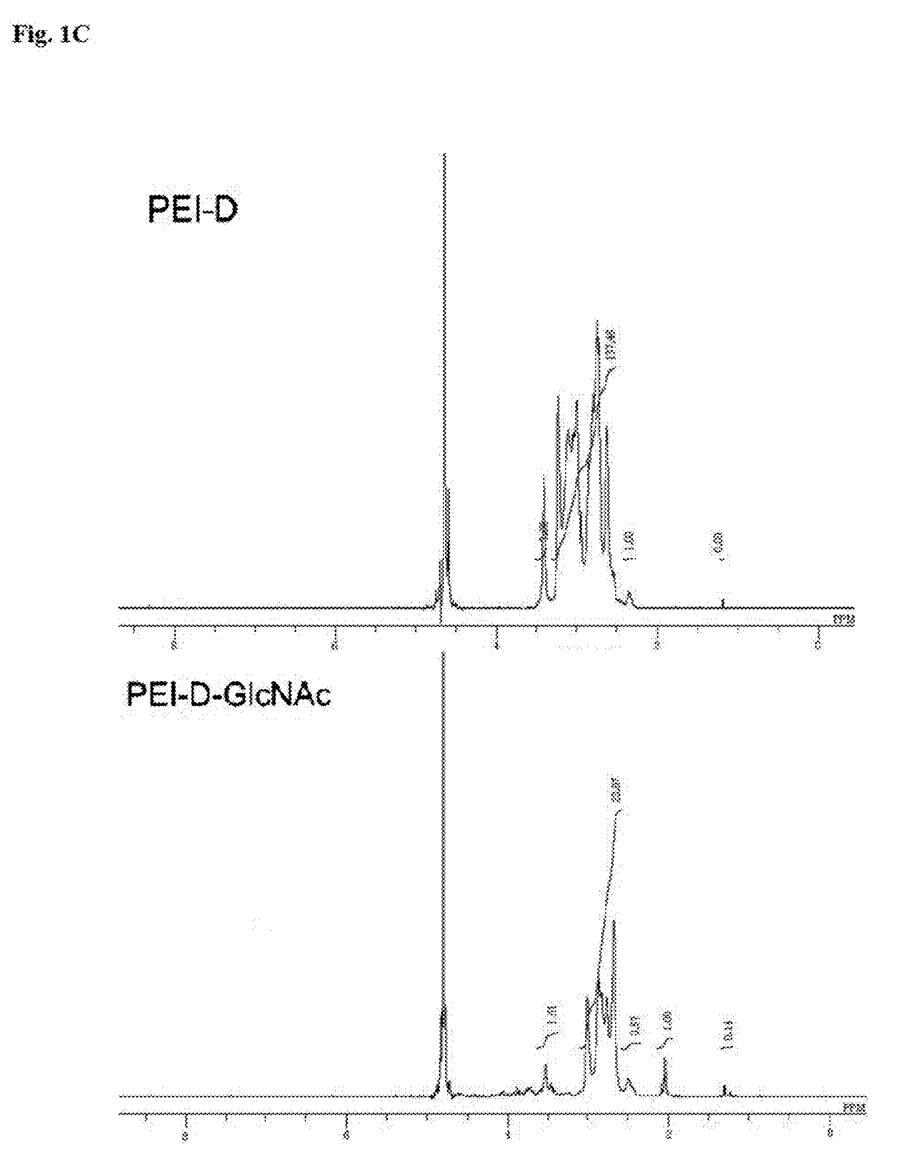
FIG. 1C shows $^1$H-NMR spectra of PEI-D and PEI-D-GlcNAc. COCH$_3$ of GlcNAc appears at 1.9 ppm, and NHCH$_2$CH$_2$ of PEI appears at 2.2-3.0 ppm.
Figure 1D:
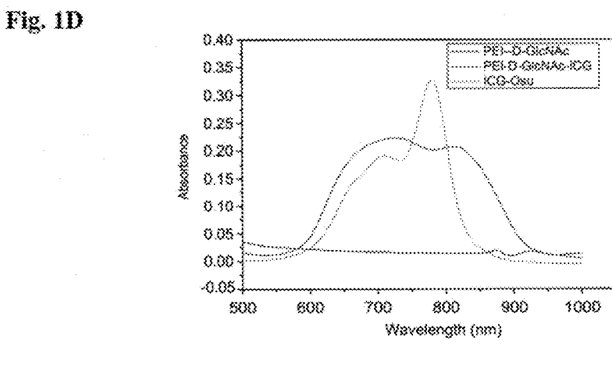
FIG. 1D shows UV spectra of PEI-D-GlcNAc and PEI-D-GlcNAc-ICG.

The disulfide bond was conjugated to polyethyleneimine (PEI) by Michael addition using cystamine bisacrylamide (CBA), to synthesize PEI-D. In Fourier transform infrared spectroscopy (FR-IR) analysis, the carbonyl group of CBA in PEI-D appeared at 1710 $cm^{-1}$ (FIG. 1B). This result indicates that the disulfide bond was successfully conjugated to PEI. The conjugation of GlcNAc to PEI was performed by the 1-ethyl-3-(3-dimethylaminopropyl)carbodiimide (EDC) coupling method. The hydroxyl group of GlcNAc was substituted with a carboxyl group and then reacted with the amino group of PEI. The immobilization of GlcNAc was confirmed by $^1$H-NMR (see FIG. 1C). The peak corresponding to the acetyl group after immobilization of GlcNAc to PEI-D appeared at 1.9 ppm. The molar ratio of GlcNAc to the primary amines in PEI was 3.5 mol % according to integration of the proton peaks in the NMR spectrum. The conjugation of ICG was analyzed by ultraviolet-visible (UV-Vis) spectroscopy (see FIG. 1D). ICG-Osu was conjugated to PEI-D-GlcNAc by covalent bonding. The absorption peak of ICG was generally found at 780 nm. However, the absorption peak of ICG in the polymer was found at 805 nm. Since several studies have reported that the absorption peak of ICG shows red shift upon conjugation to a carrier, it is thought, in the present description, that shifting of the absorbance peak occurred due to conjugation of ICG-Osu to PEI.

(Characterization of Complex and Effect of DTT)

Figure 2B:
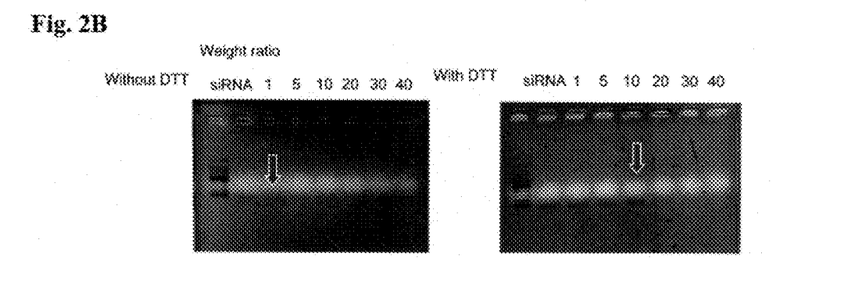
FIG. 2B shows photographs showing results of a gel shift assay by agarose gel electrophoresis of the complex in the presence of DTT (right) and in the absence of DTT (left).
Figure 3B:
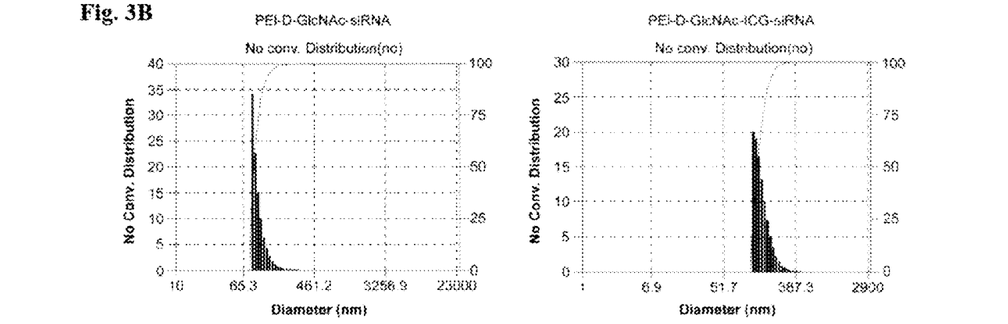
FIG. 3B shows the sizes and the size distributions of complexes (PEI-D-GlcNAc-siRNA and PEI-D-GlcNAc-ICG-siRNA) obtained by DLS calculation.
Figure 3C:
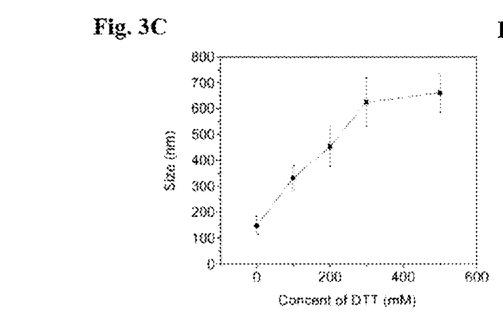
FIG. 3C shows changes in the size of the complex caused by addition of DTT.
Figure 3D:
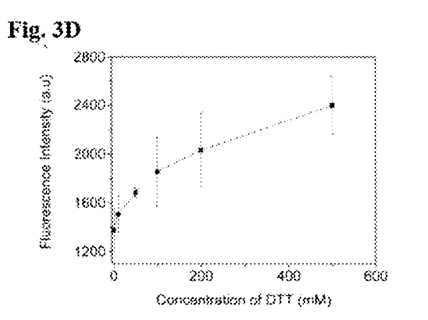
FIG. 3D shows changes in the fluorescence intensity caused by addition of DTT.

The cationic polymer and the negatively charged siRNA easily aggregated due to electrostatic interaction (see FIG. 2A). Formation of the complex between the polymer and the siRNA was confirmed by a gel shift assay (see FIG. 2B). PEI-D-GlcNAc completely aggregated with the siRNA at weight ratios of not less than 1. It was shown that therapy with 50 mM DTT allows formation of the complex at a weight ratio of not less than 10, and that the siRNA is released by destruction of the disulfide bond in the presence of a reducing agent. The shape and the size of the complex (PEI-D-GlcNAc-siRNA) were observed by TEM (see FIG. 3A). The complex had a uniform nanoparticulate shape, and its size was about 50 nm. The size and the zeta potential of the complex were investigated by DLS (see FIG. 3B). At a weight ratio of 20, the size of the complex was 97.6±21.9 nm, and the zeta potential was 28.86±4.13 mV. The size determined by DLS was larger than that determined by the TEM analysis. This is because the size determined by DLS is the hydrodynamic diameter, while the size determined by TEM is the diameter of the core alone. After the conjugation of ICG with siRNA, the size of the complex (PEI-D-GlcNAc-ICG-siRNA) increased to 148±35 nm. As shown in FIG. 3C, the size of the complex also increased by the addition of DTT. The fluorescence intensity of ICG in the complex was measured using a microplate reader at excitation and emission wavelengths of 805 nm and 820 nm, respectively (see FIG. 3D). The fluorescence intensity increased as the concentration of DTT increased. The fluorescence intensity of the complex in 500 mM DTT was approximately twice as high as the fluorescence intensity in the absence of DTT. These results also indicate that the disulfide bond was destroyed by the therapy with a reducing agent, causing release of ICG and the siRNA. Efficient gene delivery requires complete aggregation of the polymer with a gene in the form of pDNA or siRNA outside the cell, as well as easy degradation of the polymer after its incorporation into the cell. The synthesized complex enabled efficient delivery of the siRNA and emission of strong fluorescence under reducing conditions in the cell.

(Cytotoxicity)

Figure 4:
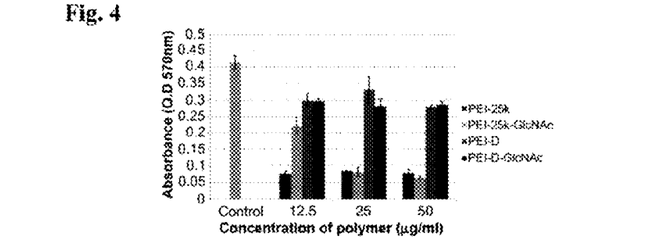
FIG. 4 is a graph showing results of investigation of the cell survival rate by an MIT assay for testing cytotoxicity of the synthesized polymers on HSCs. The data are shown as the mean±standard deviation (n=3).

Cytotoxicity of the complex to HSCs was investigated by an MTT assay. The polymer at various concentrations was incubated together with HSCs in a medium supplemented with 10% FBS for 24 hours. The present inventors previously reported that conjugation of GlcNAc to 25-KDa PEI (PEI 25 k) reduces cytotoxicity. However, PEI 25 k-GlcNAc had cytotoxicity at high concentration. The disulfide bond- and GlcNAc-conjugated PEI had lower cytotoxicity than PEI 25 k (see FIG. 4). PEI-D-GlcNAc showed high cellular viability even after the therapy at high concentration. PEI-25 k is well known as an efficient carrier for gene delivery since it has many primary amine groups that contribute to binding with negatively charged genes. However, because of its cationic nature and high molecular weight, PEI-25 k shows high cytotoxicity. Conjugation of a disulfide bond to low-molecular-weight PEI reduces the cytotoxicity by degradation of the disulfide bond under reducing conditions. These results indicate that PEI-D-GlcNAc is a safe gene carrier for HSCs.

(Cellular Uptake, and Western Blotting)

Figure 5A:
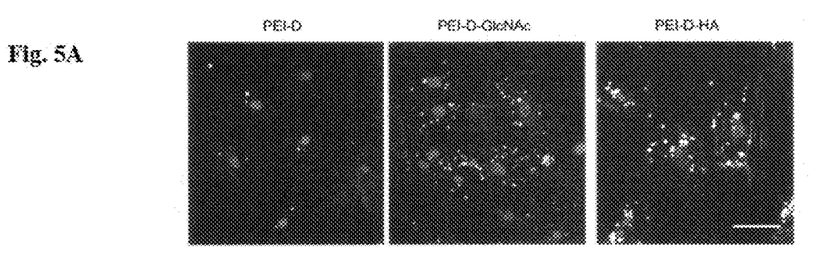
FIG. 5A shows fluorescence images observed by confocal microscopy, which images show interaction between the complexes and intracellular desmin.
Figure 5B:
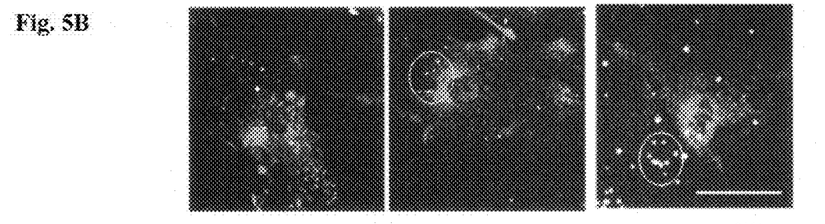
FIG. 5B shows fluorescence images observed by confocal microscopy, which images show interaction between the complexes and desmin on the cell surface of HSCs. In the fluorescence images A and B, desmin is shown in red; FITC-conjugated siRNA is shown in green; and DAPI is shown in blue.

FITC-conjugated siRNA (FITC-siRNA) was used to observe cellular uptake of the complex. A complex between the FITC-siRNA and the polymer at a weight ratio of 20 was incubated with HSCs in a medium supplemented with 10% fetal bovine serum (FBS) for 4 hours. As shown in FIG. 5A, transfection of the siRNA using PEI-D-GlcNAc allowed more effective introduction of the gene into the cells than transfection using PEI-D alone. It is thought that activated HSCs, which strongly expressed vimentin and desmin, interacted with the GlcNAc moiety in the complex between the cationic polymer and siRNA (polyplex). In fact, the PEI-D-GlcNAc/FITC-siRNA complex was present in desmin-positive regions in the cells. However, the PEI-D/FITC-siRNA complex did not interact with desmin, and only interacted with cells because of the cationic nature of PEI. In particular, the GlcNAc moiety of the complex bound to desmin that was exposed on the surface of HSCs (see FIG. 5B). Another group reported that a hyaluronic acid (HA)-conjugated gene carrier was efficiently targeted to HSCs (Kim K S., et al., ACS Nano 2010. 4: 3005-14; Park K., et al., Biomaterials 2011. 32: 4951-8). The present results showed that PEI-D-HA is also incorporated into HSCs in a large amount. However, the PEI-D-HA/FITC-siRNA complex bound not only to desmin-positive regions but also to desmin-negative regions in the cells. HA specifically binds to CD44 and hyaluronan receptor-1. Therefore, it is thought that HA was targeted not only to HSCs but also to other hepatocytes such as sinusoidal endothelial cells. Since liver fibrosis is associated with activated HSCs, gene delivery that is specifically targeted to activated HSCs may cause less side effects. The GlcNAc-immobilized carrier can be more specifically targeted to HSCs overexpressing vimentin and desmin than to other nonparenchymal cells expressing only vimentin.

Figure 5C:
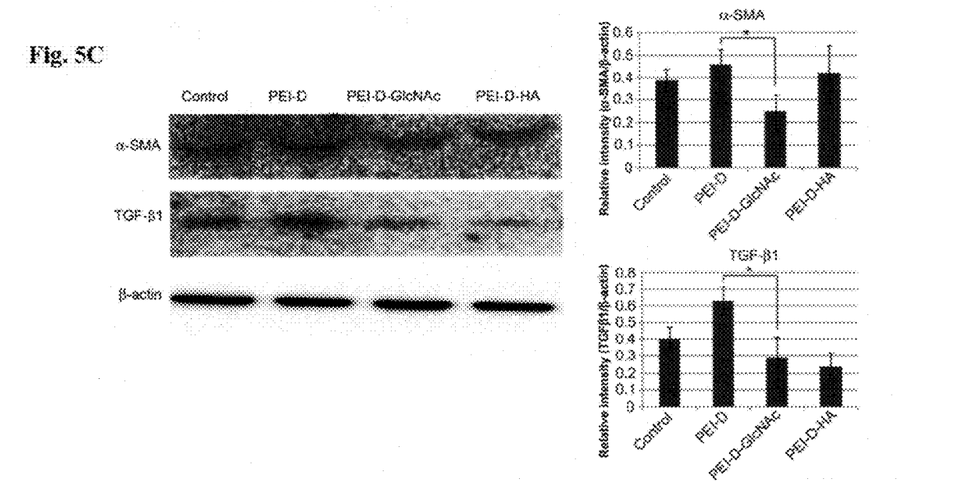
In FIG. 5C, the left panel shows photographs showing analysis results obtained by Western blotting of α-SMA and TGFβ1 after transfection with siTGF/β1 using the complexes (scale bar: 50 μm). The right panels show graphs showing results of densitometer analysis of the relative intensity of each of α-SMA and TGFβ1 bands with respect to the β-actin band (p<0.05).

To investigate the effect of siRNA therapy, transfection of HSCs with a transforming growth factor-1 (TGFβ1) siRNA in an FBS-free medium was carried out for 4 hours. Protein knock-down was measured by Western blotting 48 hours after the transfection. In the case where the PEI-D-GlcNAc/TGFβ1 siRNA complex was used, the TGFβ31 protein level in the medium was lower than those in the case of a control and the case where a PEI-D/TGFβ1 siRNA was used. When the liver is damaged, liver sinusoidal endothelial cells and Kupffer cells secrete cytokines to activate HSCs, causing phenotypic changes in the HSCs. By this, the HSCs become α-SMA-positive myofibroblast-like cells. ECM-constituting factors such as collagen are also produced, and the liver finally becomes fibrotic. TGFβ1 is an important cytokine in liver fibrosis, and knock-down of TGFβ1 causes reduction in α-SMA. The amount of reduction in α-SMA protein was larger in the case where the PEI-D-GlcNAc/TGFβ1 siRNA complex was used than in the case where the PEI-D/TGFβ1 siRNA complex was used (see FIG. 5C). These results indicate that the PEI-D-GlcNAc/TGFβ1siRNA complex was efficiently targeted to HSCs, and that a therapeutic effect was produced by efficient release of the siRNA into the cytoplasm.

(Imaging of Liver Fibrosis Using Nanocomplex)

Figure 6A:
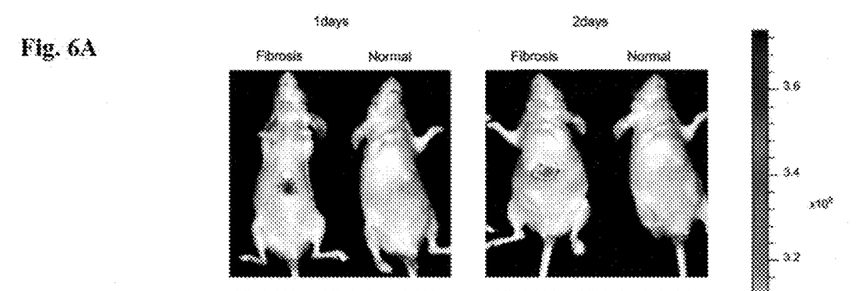
FIG. 6A shows optical images of mice with liver fibrosis (Fibrosis) and normal mice (Normal) after administration of PEI-D-GlcNAc-ICG.
Figure 6B:
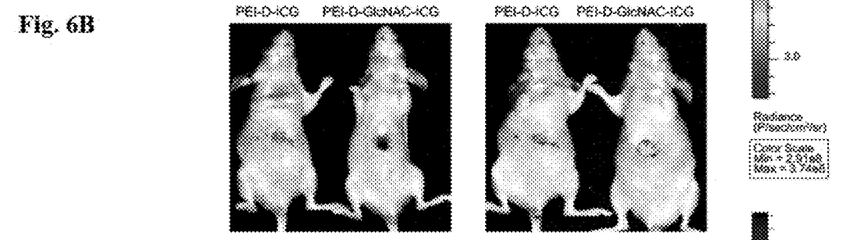
FIG. 6B shows optical images of mice with liver fibrosis after injection of PEI-D-ICG or PEI-D-GlcNAc-ICG.
Figure 6C:
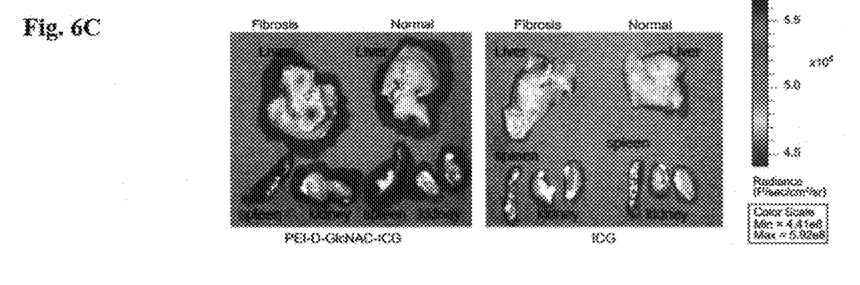
FIG. 6C shows ex vivo fluorescence images of organs (liver, spleen and kidney). The left panel shows images obtained 6 days after administration of PEI-D-GlcNAc-ICG, and the right panel shows images obtained 6 days after administration of ICG alone.
Figure 7A:
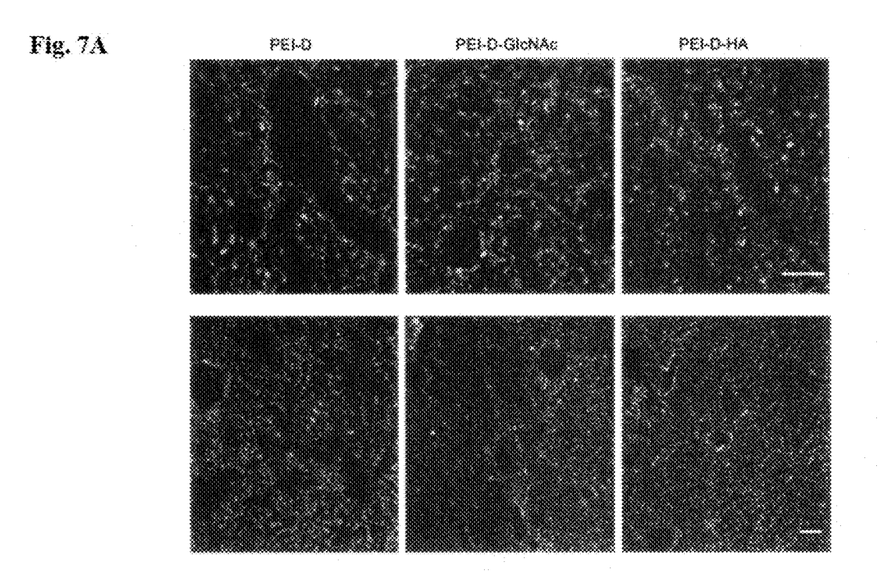
FIG. 7A shows photographs showing results of immunohistochemical analysis of liver cryosections by confocal microscopy after administration of PEI-D-GlcNAc-ICG, PEI-D-ICG or PEI-D-HA-ICG. In the photographs, desmin is shown in green; ICG is shown in red; and DAPI is shown in blue.
Figure 7B:
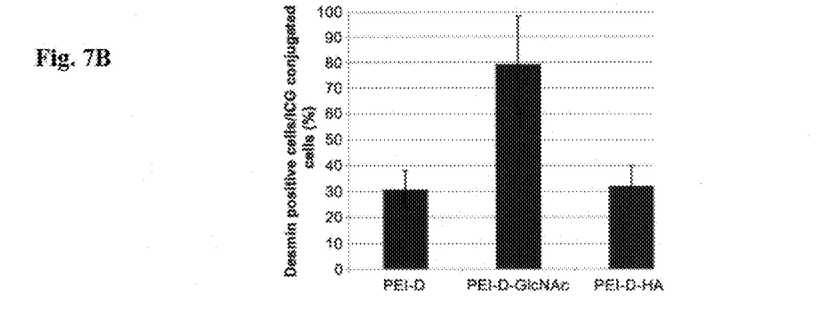
FIG. 7B is a graph showing the ratio of desmin-positive cells to ICG-introduced cells. The results are presented as the mean±standard deviation for 10 separate areas in each sample.

Liver fibrosis was observed using the ICG-conjugated complex. Fibrosis was induced in mice using carbon tetrachloride, and the induction was confirmed by histological analysis using hematoxylin and eosin staining (H&E staining). After injection of the PEI-D-GlcNAc-ICG/siRNA complex to the tail vein of normal mice and mice with liver fibrosis, the complex was first localized in the liver. On the next day, the fluorescence signal from the complex was observed only in the fibrotic mice, and the signal disappeared in the normal mice (see FIG. 6A). Moreover, two days after the injection, the PEI-D-GlcNAc-ICG/siRNA complex showed a stronger fluorescence signal than the PEI-D-ICG/siRNA complex in the mice with liver fibrosis (see FIG. 6B). In an ex vivo study, normal mice and mice with liver fibrosis were dissected 6 days after injection, and the liver, spleen, and kidney were removed. As shown in FIG. 6C, the PEI-D-GlcNAc-ICG/siRNA complex showed strong localization only in the fibrotic liver, whereas no accumulation was found in the liver of the normal mice. In the case of injection of ICG alone, no fluorescence signal was detected in either the normal mice or the mice with liver fibrosis. ICG is generally used for diagnosis of diseases, but quick quenching of its fluorescence signal has long been a major problem in imaging of disease states. The PEI-D-GlcNAc-ICG/siRNA complex was retained longer than the ICG alone only in the mice with liver fibrosis. Thus, it is thought that the long-lasting fluorescence signal of the PEI-D-GlcNAc-ICG/siRNA complex may enable more stable diagnosis of liver fibrosis. In order to study whether HSCs, which are deeply associated with liver fibrosis, interact with the PEI-D-GlcNAc-ICG/siRNA complex, immunostaining was performed. As shown in FIG. 7A, the PEI-GlcNAc-D-ICG/siRNA complex interacted with almost all desmin-positive HSCs. However, the PEI-D-ICG/siRNA complex and the PEI-D-HA-ICG/siRNA complex showed co-localization not only with HSCs but also with other cells. By calculation of the ratio of desmin-positive cells to ICG-fluorescent cells, it was found that, after injection of the PEI-D-GlcNAc-ICG/siRNA nanocomplex, 79% of the total ICG-positive cells were HSCs. In contrast, 30% and 32% of ICG-positive cells were HSCs after injection of the PEI-D-ICG/siRNA complex and the PEI-D-HA-ICG/siRNA complex, respectively (see FIG. 7B). From these results, it is thought that the PEI-D-GlcNAc-ICG/siRNA complex interacts almost exclusively with the HSCs associated with liver fibrosis, allowing selective delivery to only the fibrotic region of the liver. ICG has been used to measure hepatic function based on its fluorescence retention rate measured 15 minutes after the injection. It is expected that the PEI-D-GlcNAc-ICG/siRNA complex may exhibit a larger difference in the fluorescence retention rate between a normal liver and a fibrotic liver even after a long period. Thus, use of the PEI-D-GlcNAc-ICG/siRNA complex allows more accurate analysis of liver fibrosis.

(Diagnosis of Liver Fibrosis Using Complex)

Figure 8A:
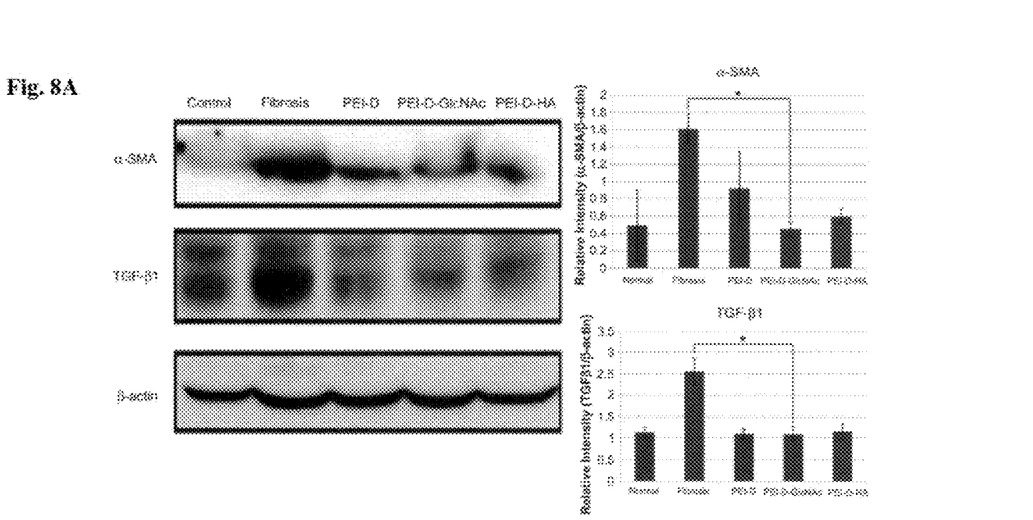
FIG. 8A shows photographs showing results obtained by Western blotting of α-SMA and TGFβ1 in the liver tissue after administration of siTGFβ1 using complexes (left panel). The right panels show graphs showing results of densitometer analysis of the relative intensity of each of α-SMA and TGFβ1 bands with respect to β-actin bands.
Figure 8B:
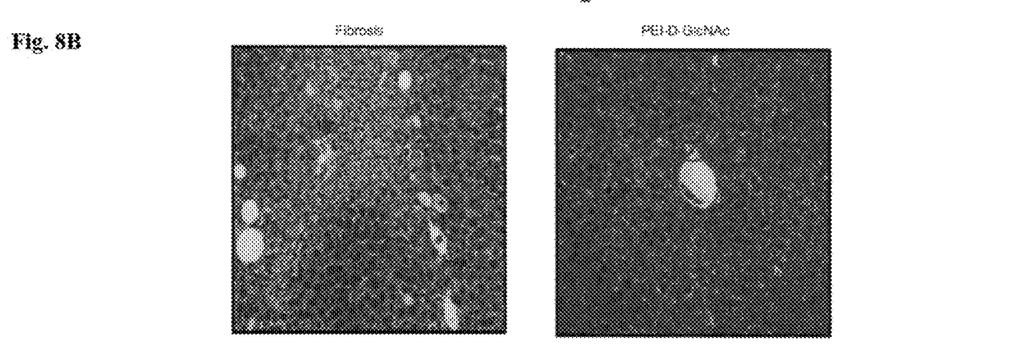
FIG. 8B shows photographs obtained by H&E staining of liver sections after administration of siTGFβ1 using PEI-D-GlcNAc (p<0.05).

Influence of TGFβ1 siRNA therapy using each complex was studied by Western blotting and H&E staining. As shown in FIG. 8A, the levels of TGFβ1 and α-SMA decreased after injection of any of the complexes (PEI-D/TGFβ1 siRNA, PEI-D-GlcNAc/TGFβ1 siRNA, and PEI-D-HA/TGFβ1 siRNA). In particular, in the case where PEI-D-GlcNAc/TGFβ1 siRNA was injected, the α-SMA level was lower than others. In contrast, the results on TGFβ1 were similar among the complexes (see FIG. 8B). In the liver, expression of α-SMA is limited to HSCs. In contrast, TGFβ1 is secreted from all hepatocytes. It was thought that transfection with the GlcNAc-immobilized complex occurred specifically in HSCs. On the other hand, it was thought that other complexes interacted with both HSCs and other cells. This may explain why the level of α-SMA was lowest in the case where PEI-D-GlcNAc/TGFββ1 siRNA was used, while the level of TGFβ1 was almost the same among all of the complexes. The level of α-SMA indicates the level of activation of HSCs. After the therapy with TGFβ1 siRNA using PEI-D-GlcNAc-ICG, the level of α-SMA remarkably decreased. This suggests the therapeutic effect on liver fibrosis.

In H&E staining, the mice with carbon tetrachloride-induced liver fibrosis showed many symptoms of inflammation. After injection of the PEI-D-GlcNAc-ICG/TGFβ1 siRNA nanocomplex, the liver tissue appeared like a normal tissue, which does not show formation of nodules (see FIG. 8B). These results indicate that the PEI-D-GlcNAc-ICG/TGFβ1 siRNA complex was effective not only for imaging but also for therapy of liver fibrosis.

It was shown, as described above, that the GlcNAc-immobilized bioreducible complex is useful for efficient imaging and therapy of liver fibrosis. Conjugation of a disulfide bond and GlcNAc to PEI decreased the cytotoxicity of PEI. The GlcNAc-immobilized nanocomplex interacted strongly with HSCs via desmin exposed on the surface. In an in vivo test, the PEI-D-GlcNAc-ICG/siRNA complex remarkably accumulated in the fibrotic liver of mice. Moreover, by immunostaining of the liver tissue, it could be confirmed that the complex interacts specifically with HSCs. It was confirmed by Western blotting and H&E staining that the levels of α-SMA and inflammation decreased after transfection with TGFβ1 siRNA using PEI-D-GlcNAc-ICG. Thus, it is thought that the PEI-D-GlcNAc-ICG/TGFβ1 siRNA complex is useful for stable and accurate diagnosis and therapy of liver fibrosis.

The invention claimed is:

1. A sugar chain-containing polymer comprising:
a polyethyleneimine with a disulfide bond located in the backbone of the polyethyleneamine; and a chemical structure extending from the backbone of the polyethyleneimine as shown below:

2. The sugar chain-containing polymer according to claim 1, further comprising a fluorescent dye bound thereto.

3. The sugar chain-containing polymer according to claim 2, wherein said fluorescent dye is indocyanine green.

4. A sugar chain-containing polymer complex comprising of the sugar chain-containing polymer according to claim 1 and an anionic substance(s).

5. The sugar chain-containing polymer complex according to claim 4, wherein said sugar chain-containing polymer and said anionic substance(s) form a complex by electrostatic interaction.

6. The sugar chain-containing polymer complex according to claim 4, wherein said anionic substance is nucleic acid.

7. The sugar chain-containing polymer complex according to claim 6, wherein said nucleic acid is RNA.

8. The sugar chain-containing polymer complex according to claim 7, wherein said RNA is an siRNA.

9. The sugar chain-containing polymer complex according to claim 8, wherein said siRNA is an siRNA of TGFβ1.

10. A sugar chain-containing polymer complex comprising of the sugar chain-containing polymer according to claim 2 and an anionic substance(s).

11. A sugar chain-containing polymer complex comprising of the sugar chain-containing polymer according to claim 3 and an anionic substance(s).

12. The sugar chain-containing polymer complex according to claim 5, wherein said anionic substance is nucleic acid.

13. The sugar chain-containing polymer complex according to claim 1, wherein the disulfide bond is introduced into the polyethyleneimine backbone by reacting N,N'-cystaminebisacrylamide with polyethyleneimine.

* * * * *